United States Patent [19]

Scott

[11] Patent Number: 5,206,017

[45] Date of Patent: Apr. 27, 1993

[54] USE OF PROTEASE NEXIN-I AS AN ANTIINFLAMMATORY

[75] Inventor: Randal A. Scott, Cupertino, Calif.

[73] Assignee: Incyte Pharmaceuticals, Inc., Palo Alto, Calif.

[21] Appl. No.: 804,332

[22] Filed: Dec. 6, 1991

Related U.S. Application Data

[63] Continuation-in-part of Ser. No. 505,442, Apr. 5, 1990, Pat. No. 5,112,608, which is a continuation-in-part of Ser. No. 25,450, Mar. 13, 1987, which is a continuation-in-part of Ser. No. 871,501, Jun. 6, 1986, abandoned, which is a continuation-in-part of Ser. No. 870,232, Jun. 3, 1986, abandoned.

[51] Int. Cl.$^5$ ............... A61K 37/547; A61K 37/54; A61K 37/00

[52] U.S. Cl. ............... 424/94.64; 424/94.63; 514/12

[58] Field of Search ............ 530/395; 424/94.67, 424/94.1, 94.63, 94.64; 514/12

[56] References Cited

U.S. PATENT DOCUMENTS

| | | | |
|---|---|---|---|
| 4,265,233 | 5/1981 | Sugitachi et al. | 128/155 |
| 4,904,469 | 2/1990 | Petereit et al. | 424/94.3 |
| 5,006,252 | 4/1991 | Scott et al. | 210/635 |
| 5,112,608 | 5/1992 | Scott et al. | 424/94.64 |

FOREIGN PATENT DOCUMENTS 0233838  8/1987  European Pat. Off. .

OTHER PUBLICATIONS

Hrubey et al, Agents and Actions, vol. 34 (1991) pp. 56–59.
Pratta et al, Agents and Actions, vol. 34 (1991) pp. 60–62.
Ganu et al, Agents and Actions, vol. 34 (1991) pp. 226–228.
Borella et al, Agents and Actions, vol. 34 (1991) pp. 220–222.
Stevens et al, Agents and Actions, vol. 34 (1991) pp. 217–219.
U.S. Department of Health and Human Services, "Arthritis, Rheumatic Diseases, and Related Disorders", (1987) pp. 1–20.
Meier et al, Letters to Nature, vol. 342 (1989) pp. 548–550.
Needels et al, Neuroscience, 18(3) 1986 pp. 517–526.
Berg et al, J. Cell Biochem Suppl., O(15 Part F) 1991 p. 192.
Gomez-Pinilla et al, Soc. Neurosci Abstr., 16(2) 1990 p. 1346.
Rudge et al, J. of Neuroscience, 10(11) 1990, pp. 3594–3603.
Ruppert et al, Matrix, 10(4) 1990, p. 246.
Scott et al, J. Biol. Chem. (1985), 260(11): pp. 7029–7034.
Eaton et al., Chem. Abstracts (1984) 101(7):244.
Gloor et al., Biol. Abstracts (1987) 83(7):792.
Erickson et al, Proc. Natl. Acad. Sci (1985) 82:8710–8714.
Ny et al, Proc. Natl. Acad. Sci (1986) 83:6776–6780.
Walsh, "Proteases in Biological Control", Reich et al., eds., (1975) Cold Spring Harbor Conf. on Cell Prol., vol. 2, p. 1–11.
Baker et al., Cell (1980) 21:37–45.
Low et al., Proc. Natl. Acad. Sci. (1981) 78(4):2340–2344.
Baker et al, The Receptors, vol. III (1985) Chapt. 5, pp. 153–172.
Scott et al, J. Biol. Chem. (1983) 258(17):10439–10444.
Guenther et al, EMBO Journal (1985) 4(8):1963–1966.
Barde et al, Nature (1978) 274:818.
Baker et al, J. Cell Physiol. (1982) 112:291–297.
Low et al, Nature (1982) 298:476–478.
Lobb, Biochemistry (1988) 27(7):2572–2578.
Jones et al, Cancer Res. (1980) 40:3222–3227.
Bergman et al., Proc. Natl. Acad.Sci. (1986) 83:996–1000.
McGuire-Goldring et al., Arth. Rheum. (1984) 27:524.
Monrad et al., Prog. Brain Res. (1983) 58:359–364.
Van Nostrand et al., Biochemistry (1988) 27:2176–2181.
McGrogan et al., Bio/Technology (1988) 6:172–177.

*Primary Examiner*—Douglas W. Robinson
*Assistant Examiner*—Susan M. Weber
*Attorney, Agent, or Firm*—Morrison & Foerster

[57] ABSTRACT

Methods and pharmaceutical compositions for treatment of inflammation and arthritis using protease nexin-I as an active ingredient are disclosed.

15 Claims, No Drawings

USE OF PROTEASE NEXIN-I AS AN ANTIINFLAMMATORY

CROSS-REFERENCE TO RELATED APPLICATIONS

This application is a continuation-in-part of U.S. Ser. No. 07/505,442, filed Apr. 5, 1990, now U.S. Pat. No. 5,112,608, which is a continuation-in-part of U.S. Ser. No. 025,450, filed Mar. 13, 1987, which is a continuation-in-part of U.S. Ser. No. 06/871,501, filed Jun. 6, 1986, now abandoned, which is a continuation-in-part of U.S. Ser. No. 06/870,232, filed Jun. 3, 1986, now abandoned.

TECHNICAL FIELD

The invention relates to the field of treatment of conditions characterized by inflammation or inflammatory responses. More specifically, it concerns treatment of inflammation and inflammatory diseases with protease nexin-1.

BACKGROUND ART

The structure and recombinant production of protease nexin-I are described in European patent application 251505, published Jan. 7, 1988, and incorporated herein by reference. The contents of this publication are substantially the same as those of above-referenced Ser. No. 07/025,450, which case is allowed and involved in an interference. As disclosed in these documents, protease nexin-I occurs naturally in two closely related forms, PN-Iα and PN-Iβ, which result from alternate splicing events in the mRNA message encoding the protein. PN-Iα and PN-Iβ consist of 378 and 379 amino acids, respectively, and differ only in that the arginyl residue at position 310 of PN-Iα is replaced by a thr-gly sequence in PN-Iβ. PN-Iα and PN-Iβ can be prepared individually using recombinant means or the natively produced protein can be isolated from various tissue sources such as human fibroblasts or glial cells. Methods for purifying protease nexin-I to apparent homogeneity from fibroblasts have been described by Scott, R. W., et al., *J. Biol Chem* (1985) 260:7029-7034.

The ability of protease nexin-I to inhibit various anti-clotting factors such as urokinase and tissue plasminogen activator is well established. It is also known that protease nexin-I stimulates the growth of neurites. It has now been demonstrated that protease nexin-I is effective in preventing degradation of connective tissue and in the treatment of inflammatory diseases such as arthritis.

DISCLOSURE OF THE INVENTION

The invention is directed to pharmaceutical compositions and methods useful in the treatment of inflammation and arthritis. The compositions may contain either PN-Iα or PN-Iβ or both, and may contain additional active ingredients as well as standard excipients. The methods of treatment involve administration of the foregoing compositions in suitable protocols for the control of these conditions. Local administration to the site of inflammation is particularly preferred.

MODES OF CARRYING OUT THE INVENTION

The conditions for which treatment with protease nexin-I is indicated include inflammation and arthritis, in particular, acute or chronic inflammation, acute or chronic arthritis. Particular conditions that may benefit from administration of the compounds of the invention include osteoarthritis, rheumatoid arthritis, degenerative arthritis, psoriatic arthritis (psoriasis), pemphigus, joint inflammation, conditions treated by collagen therapy, juvenile arthritis, ankylosing spondylitis, inflammatory bowel disease, sepsis, emphysema, adult respiratory distress syndrome (ARDS) and septic joints.

Inflammation may occur from a variety of causes and is evidenced by swelling and reddening at the inflamed location or can comprise an overall physiological response characterized by pain and fever. Depending on the nature of the condition, either systemic or local administration of protease nexin-1 compositions is employed. A preferred means of administration is by injection; suitable dosage ranges are of the order of 0.1-1000 mg per injection daily, preferably 1-10 mg per injection daily. For injection, the protease nexin is formulated into a liquid formulation or a solid which can be reconstituted as a suspension or solution. Suitable excipients for use in injection include physiological saline, Hank's solution, Ringer's solution, and the like. Additional excipients such as stabilizers, buffers, solubilizing agents and the like can also be included. Suitable modes for injection include intravenous, intramuscular, subcutaneous, peritoneal and, as described herein, localized treatment. The protocol may involve a single injection or multiple doses at spaced intervals. Multiple doses may be identical in level or may differ according to design optimization parameters which can be routinely determined. Similar protocols are useful in treating arthritic subjects although the treatment in these cases is more likely to extend over prolonged periods due to the chronic nature of this condition.

For inflammation focused at particular locations, localized administration at the site is preferred. It is desirable to obtain levels at the inflammation site of 10-100 μg/ml PN-I.

Suitable routes of systemic administration, besides injection, also include transdermal, transmucosal, or oral administration.

Transmucosal administration takes advantage of the ability of certain excipients to cause the active ingredient protease nexin-I to cross mucosal barriers. Transmucosal administration generally requires less disruption of tissue than does transdermal administration which is known to require specialized effectors. Suitable materials to effect the transmucosal passage of protease nexin-I include certain steroids such as bile salts and fusidic acid derivatives, as well as additional detergents such as laurates or aromatic sulfonates. Transmucosal administration may be by, for example, aerosol delivery to the nasal passages, by suppository, or transbuccal dosages. Transdermal administration is more difficult, and generally through skin patches such as those placed behind the ear or in other skin areas which are relatively unresistant to the passage of materials.

Oral administration is also difficult, but not impossible when the compounds are properly formulated to prevent their degradation in the digestive tract. Various enteric compositions are known which may assure the passage of the protease nexin-I into the blood stream without degradation in the stomach.

All of the foregoing may be adapted to provide PN-I localized to the site of inflammation in the case of, for example, inflamed joints, local trauma, or digestive tract inflammation.

Preferably, the protease nexin-I is provided in unit dosage form for easy administration in the devised protocol.

The following examples are intended to illustrate but not to limit the invention.

EXAMPLE

Inhibition of Glycosaminoglycan (GAG) Loss by PN-I

A model for arthritis in rabbits is constructed as follows: the right knee of anesthetized Pasteurella-free New Zealand white rabbits was injected with a single dose of either recombinant human IL-1 (Amgen, specific activity $5 \times 10^8$ U/mg and recombinant human serine analog bFGF (Fox, G. M., et al., *J Biol Chem* (1988) 263:18452-18458) alone or in combination. The left knee was injected with an equal volume of vehicle as a contralateral control. At various times after injection, the rabbits were euthanized, and each knee joint was rinsed with 1 ml saline. The fluid was assayed for cell infiltration by microscopic examination and for glycosaminoglycan (GAG) content by the assay of Farndale, R. W., et al., *Biochem Biophys Acta* (1986) 883:173-177. The knees were removed, the cartilage scraped from the tibial plateau, and the cartilage digested overnight at 65° C. with papain. The GAG is reported as $\mu$g/mg by weight of cartilage.

In this assay, various doses of PN-I or vehicle were given intraarticularly to the right knees for four days, one day before induction of arthritic conditions by IL-1/FGF, and then daily for three additional days. The inducing dosages of bFGF and IL-1 were 10 $\mu$ and 10,000 units, respectively.

In a series of controlled experiments, treatment with PN-I consistently showed prevention of GAG loss as compared to control.

In one series of experiments, PN-I treatment at 2.5 mg/day resulted in only a 19% GAG loss as compared to 31% loss of GAG in the control (p=0.05).

In a second series of experiments, PN-I treatment at 2 mg/day resulted in only a 23% loss in GAG as compared to 45% in the control (p<0.001). In a third protocol, dosages of 0.5 mg/day and 1 mg/day resulted in 37% and 38% losses, respectively, as compared to 41% loss of GAG in the control. Thus, PN-I consistently reversed the arthritic effect of the bFGF/IL-1 stimulation. Administration of 2.5 mg cytochrome c had no effect.

I claim:

1. A method of reducing the loss of glycosaminoglycans in connective tissue of a patient suffering from a disease which causes the loss of glycosaminoglycans from connective tissue, comprising administering to the patient an amount of protease nexin-I sufficient to reduce the loss of glycosaminoglycans from connective tissue.

2. The method of claim 1, wherein the protease nexin-I is administered by injection.

3. The method of claim 1, wherein the protease nexin-I is administered as a pharmaceutical composition comprised of protease nexin-I dispersed in a pharmaceutically acceptable carrier.

4. The method of claim 1, wherein the protease nexin-I is administered locally to a site determined to be undergoing a loss of glycosaminoglycans.

5. The method as claimed in claim 1, wherein the protease nexin-I is protease nexin-I$\alpha$.

6. The method as claimed in claim 1, wherein the protease nexin-I is protease nexin-I$\beta$.

7. The method as claimed in claim 1, wherein the protease nexin-I is administered in an amount in the range of 0.1-1,000 mg.

8. The method as claimed in claim 7, wherein the protease nexin-I is administered in an amount in the range of 1-10 mg.

9. The method as claimed in claim 1, wherein the disease which causes loss of glycosaminoglycans in connective tissue is arthritis.

10. The method as claimed in claim 9, wherein the arthritis is a type of arthritis selected from the group consisting of osteoarthritis, rheumatoid arthritis, degenerative arthritis, psoriatic arthritis, and juvenile arthritis.

11. A method of reducing inflammation comprising administering to the patient an amount of protease nexin-I sufficient to reduce the loss of glycosaminoglycans from connective tissue and thereby reduce inflammation.

12. The method of claim 11, wherein the protease nexin-I is administered by injection in an amount in the range of 1-10 mg.

13. The method of claim 11, wherein the protease nexin-I is administered as a pharmaceutical composition comprised of protease nexin-I dispersed in a pharmaceutically acceptable carrier and administered in an amount in the range of 0.1-1,000 mg.

14. The method of claim 11, wherein the protease nexin-I is administered in combination with a pharmaceutically acceptable carrier to the site of inflammation.

15. A method of reducing inflammation and the loss of glycosaminoglycans in connective tissue of a patient suffering from arthritis, comprising administering to the patient, by injection, an amount of protease nexin-I sufficient to reduce the loss of glycosaminoglycans from connective tissue and thereby reduce inflammation.

* * * * *